(12) United States Patent
Stuckey

(10) Patent No.: US 11,577,038 B2
(45) Date of Patent: Feb. 14, 2023

(54) ENDOTRACHEAL TUBE TO BAG VALVE DEVICE CONNECTING ASSEMBLY

(71) Applicant: Will Stuckey, Snohomish, WA (US)

(72) Inventor: Will Stuckey, Snohomish, WA (US)

(*) Notice: Subject to any disclaimer, the term of this patent is extended or adjusted under 35 U.S.C. 154(b) by 830 days.

(21) Appl. No.: 16/508,994

(22) Filed: Jul. 11, 2019

(65) Prior Publication Data

US 2021/0008314 A1 Jan. 14, 2021

(51) Int. Cl.
*A61M 16/04* (2006.01)
*A61M 16/20* (2006.01)
*A61M 39/10* (2006.01)
*A61M 16/00* (2006.01)

(52) U.S. Cl.
CPC .... *A61M 16/0463* (2013.01); *A61M 16/0084* (2014.02); *A61M 16/208* (2013.01); *A61M 39/1055* (2013.01); *A61M 2039/1016* (2013.01); *A61M 2039/1027* (2013.01)

(58) Field of Classification Search
CPC .............. A61M 16/0084; A61M 16/04; A61M 16/0463; A61M 16/0816; A61M 16/208; A61M 39/1055; A61M 2039/1016; A61M 2039/1027
See application file for complete search history.

(56) References Cited

U.S. PATENT DOCUMENTS

| | | | |
|---|---|---|---|
| 4,915,418 A | 4/1990 | Palatchy | |
| 5,329,921 A | 7/1994 | Socaris | |
| 5,540,221 A * | 7/1996 | Kaigler | A61M 16/12 128/205.13 |
| 5,555,881 A * | 9/1996 | Rogers | A61M 25/02 128/207.14 |
| 5,679,884 A | 10/1997 | Kirk | |
| 5,996,579 A | 12/1999 | Coates | |
| 7,140,370 B2 | 11/2006 | Tresnak | |
| D638,931 S | 5/2011 | Graham | |
| 8,770,190 B2 * | 7/2014 | Doherty | A61M 16/0875 128/200.24 |
| 9,169,952 B2 * | 10/2015 | Horgan | F16B 5/0275 |
| 10,010,690 B1 | 7/2018 | Geraghty | |
| 10,327,997 B2 * | 6/2019 | Griffith | A61J 15/0065 |
| 11,298,496 B2 * | 4/2022 | Mansi | A61M 16/04 |
| 2009/0308397 A1 * | 12/2009 | Neame | A61M 16/0488 128/207.17 |
| 2015/0352303 A1 | 12/2015 | Godwin | |
| 2021/0138174 A1 * | 5/2021 | Nelson | A61M 16/0833 |

* cited by examiner

*Primary Examiner* — Colin W Stuart
*Assistant Examiner* — Matthew D Ziegler

(57) ABSTRACT

An endotracheal tube to bag valve device connecting assembly for quick access to an endotracheal tube for suctioning includes a first tube and a second tube that are coupled to a hinge so that the first tube is positioned to be swiveled relative to the second tube to align the first tube with the second tube, wherein the first tube and the second tube define a pipe. A first end of the pipe is configured to selectively couple to a patient valve of a bag valve device. A second end of the pipe is configured to selectively couple to an endotracheal tube. The pipe is configured to allow flow of gas from the bag valve device to the endotracheal tube. The first tube is positioned to be swiveled on the hinge so that the second tube is configured to insert a suction tube into the endotracheal tube to clear an airway.

13 Claims, 5 Drawing Sheets

ENDOTRACHEAL TUBE TO BAG VALVE DEVICE CONNECTING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relate to connecting assemblies and more particularly pertains to a new connecting assembly for quick access to an endotracheal tube for suctioning.

BRIEF SUMMARY OF THE INVENTION

An embodiment of the disclosure meets the needs presented above by generally comprising a first tube and a second tube that are coupled to a hinge so that the first tube is positioned to be swiveled relative to the second tube to align the first tube with the second tube, wherein the first tube and the second tube define a pipe. A first end of the pipe is configured to selectively couple to a patient valve of a bag valve device. A second end of the pipe is configured to selectively couple to an endotracheal tube. The pipe is configured to allow flow of gas from the bag valve device to the endotracheal tube. The first tube is positioned to be swiveled on the hinge so that the second tube is configured to insert a suction tube into the endotracheal tube to clear an airway.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
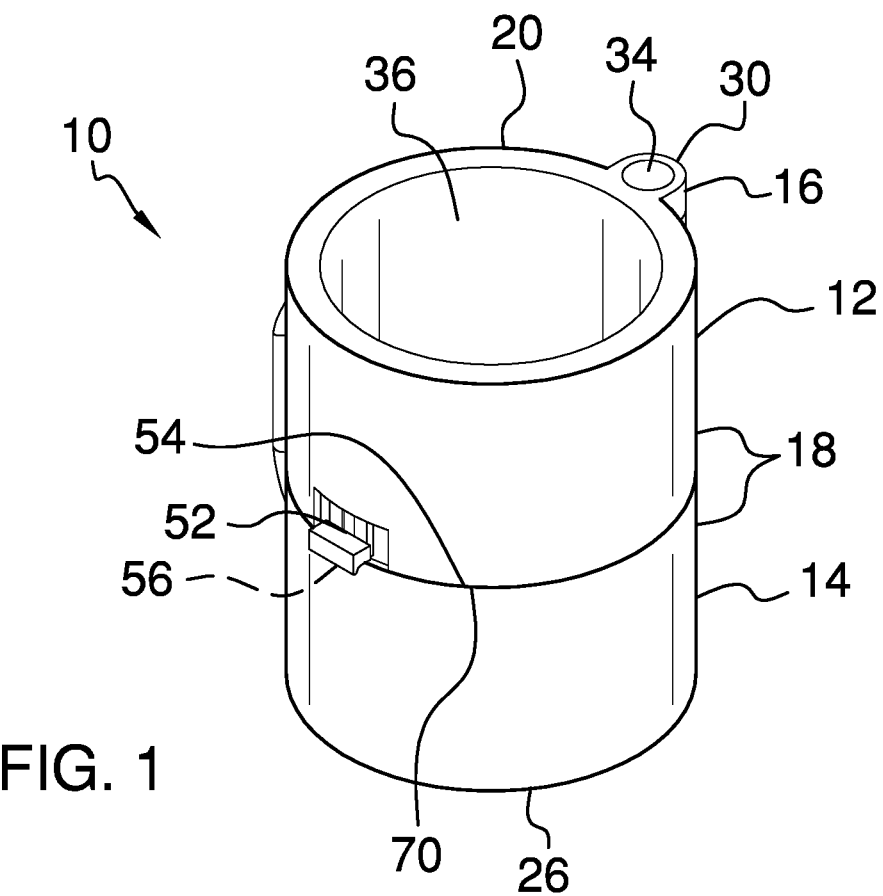
FIG. 1 is an isometric perspective view of an endotracheal tube to bag valve device connecting assembly according to an embodiment of the disclosure.
Figure 2:
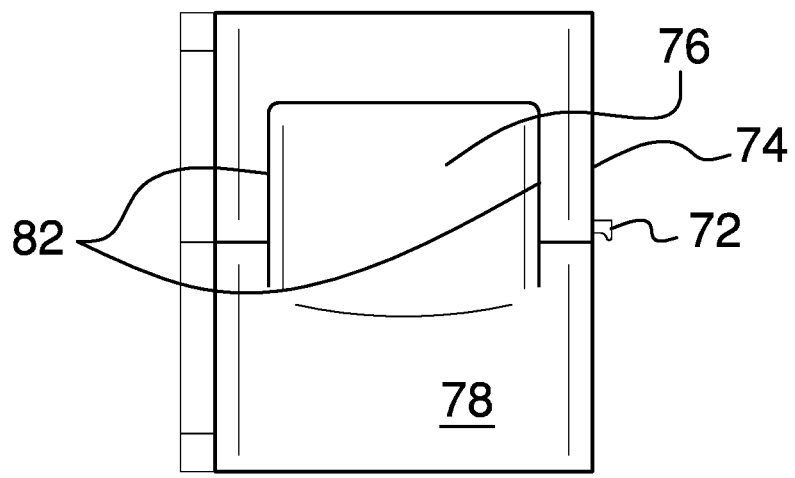
FIG. 2 is a side view of an embodiment of the disclosure.
Figure 3:
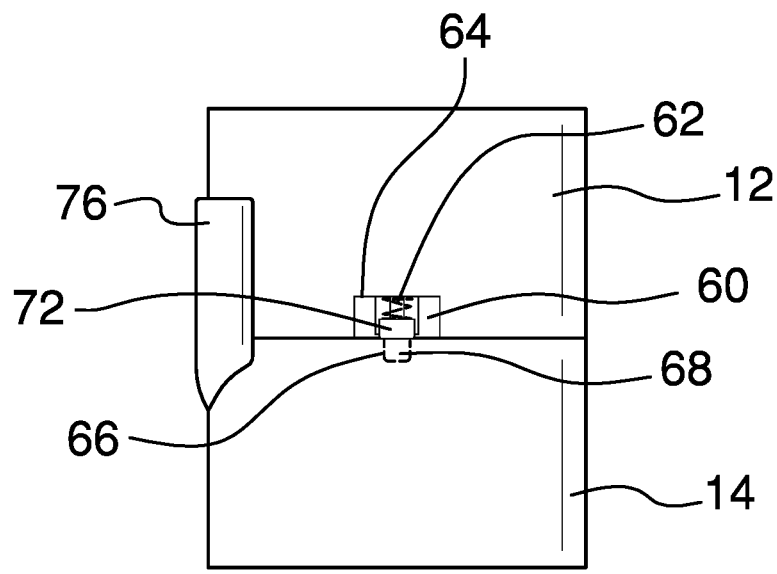
FIG. 3 is a front view of an embodiment of the disclosure.
Figure 4:
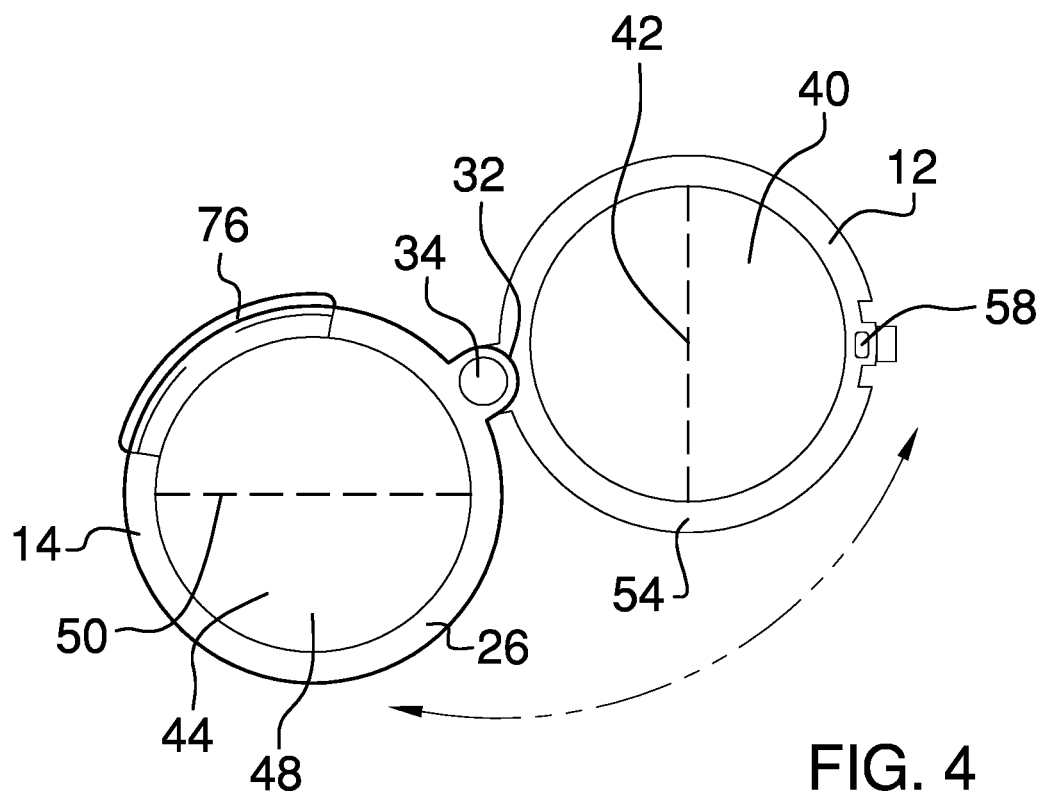
FIG. 4 is a bottom view of an embodiment of the disclosure.
Figure 5:
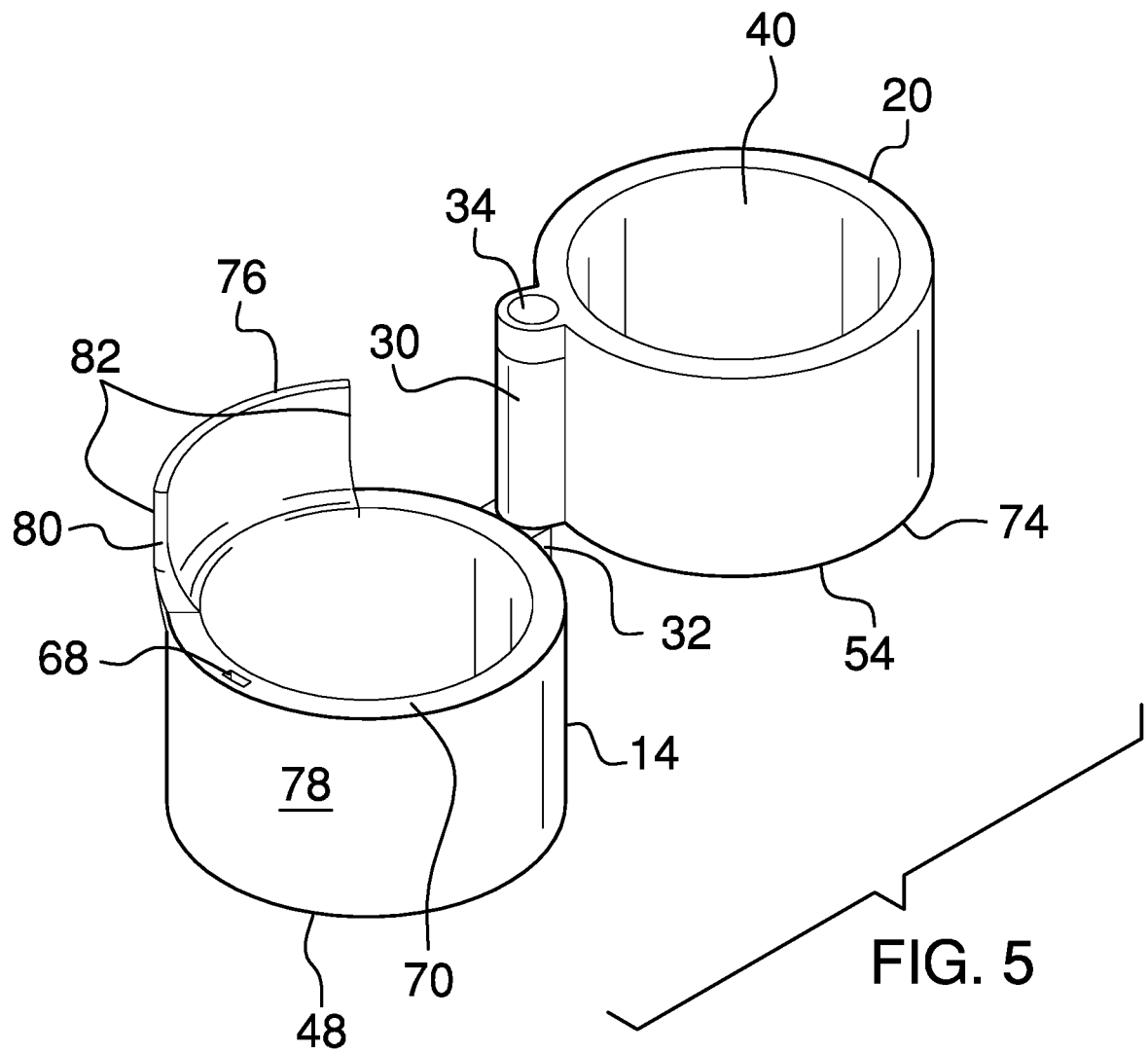
FIG. 5 is a detail view of an embodiment of the disclosure.

With reference now to the drawings, and in particular to FIGS. 1 through 7 thereof, a new connecting assembly embodying the principles and concepts of an embodiment of the disclosure and generally designated by the reference numeral 10 will be described.

As best illustrated in FIGS. 1 through 7, the endotracheal tube to bag valve device connecting assembly 10 generally comprises a first tube 12 and a second tube 14 that are coupled to a hinge 16 so that the first tube 12 is positioned to be swiveled relative to the second tube 14 to align the first tube 12 with the second tube 14, wherein the first tube 12 and the second tube 14 define a pipe 18. A first end 20 of the pipe 18 is configured to selectively couple to a patient valve 22 of a bag valve device 24. A second end 26 of the pipe 18 is configured to selectively couple to an endotracheal tube 28. The pipe 18 is configured to allow flow of gas from the bag valve device 24 to the endotracheal tube 28. The first tube 12 is positioned to be swiveled on the hinge 16 so that the second tube 14 is configured to insert a suction tube into the endotracheal tube 28 to clear an airway.

The hinge 16 comprises a first barrel 30, a second barrel 32, and a pivot 34, or other hinging means, such as, but not limited to, a pivot hinge, and the like. The first barrel 30 is coupled to the first tube 12. The second barrel 32 is coupled to the second tube 14. The pivot 34 extends through the first barrel 30 and the second barrel 32 so that the first tube 12 is hingedly coupled to the second tube 14.

A first coupler 36 is coupled to the first end 20 of the pipe 18. The first coupler 36 is complementary to an associated connector 38 of the patient valve 22 of the bag valve device 24. The first coupler 36 is configured to be selectively coupled to the associated connector 38 to couple the pipe 18 to the bag valve device 24. The first coupler 36 comprises a first socket 40 that has an inner diameter 42 of from 5.0 to 75.0 millimeters. The first socket 40 may have an inner diameter 42 of from 10.0 to 25.0 millimeters. The first socket 40 may have an inner diameter 42 of 15.0 millimeters.

A second coupler 44 is coupled to the second end 26 of the pipe 18. The second coupler 44 is complementary to an associated connector 46 of the endotracheal tube 28. The second coupler 44 is configured to be selectively coupled to the associated connector 46 to couple the pipe 18 to the endotracheal tube 28. The second coupler 44 comprises a second socket 48 that has an internal diameter 50 of from 5.0 to 75.0 millimeters. The second socket 48 may have an internal diameter 50 of from 10.0 to 25.0 millimeters. The second socket 48 may have an internal diameter 50 of 15.0 millimeters.

A first fastener 52 is coupled to a lower end 54 of the first tube 12. A second fastener 56 is coupled to an upper end 70 of the second tube 14. The second fastener 56 is complementary to the first fastener 52 so that the second fastener 56 is positioned to selectively couple to the first fastener 52 to fixedly couple the second tube 14 to the first tube 12 to define the pipe 18. The second fastener 56 and the first fastener 52 comprise a clasp 58, or other fastening means, such as, but not limited to, a latch, a clip, and the like.

The clasp 58 is spring-loaded and comprises a recess 60 that extends into the first tube 12 adjacent to the lower end 54. A spring 62 is coupled to the first tube 12 and extends from an upper limit 64 of the recess 60. A pin 66 is coupled to the spring 62 distal from the upper limit 64. A channel 68 extends into the second tube 14 from the upper end 70 so that the channel 68 is aligned with and positioned to selectively insert the pin 66. A knob 72 is coupled to the pin 66 proximate to the spring 62 so that the knob 72 extends from the recess 60 past a circumference 74 of the first tube 12. The knob 72 is configured to be engaged by a digit of a hand of a user to extract the pin 66 from the channel 68, positioning the user to swivel the first tube 12 relative to the second tube 14 so that the second tube 14 is configured to insert the suction tube into the endotracheal tube 28 to clear the airway.

A protrusion 76 is coupled to an exterior surface 78 of the second tube 14 proximate to the upper end 70. The protrusion 76 extends past the upper end 70 and is configured to guide the suction tube into the endotracheal tube 28. A bevel 80 is positioned in a respective opposing side 82 of the protrusion 76 so that the respective opposing side 82 is configured the suction tube to allow slide along the bevel 80 into the endotracheal tube 28.

Figure 6:
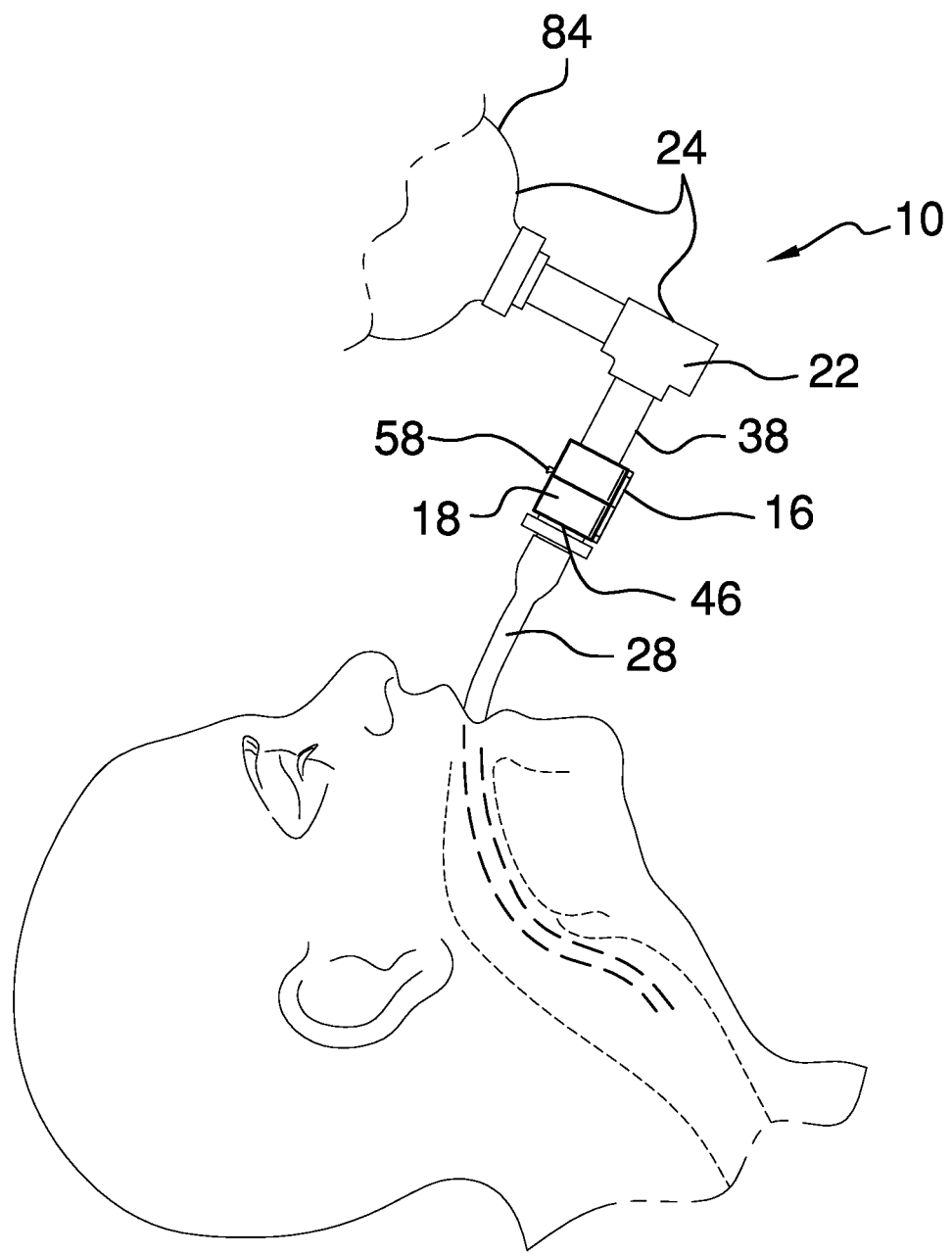
FIG. 6 is an in-use view of an embodiment of the disclosure.
Figure 7:
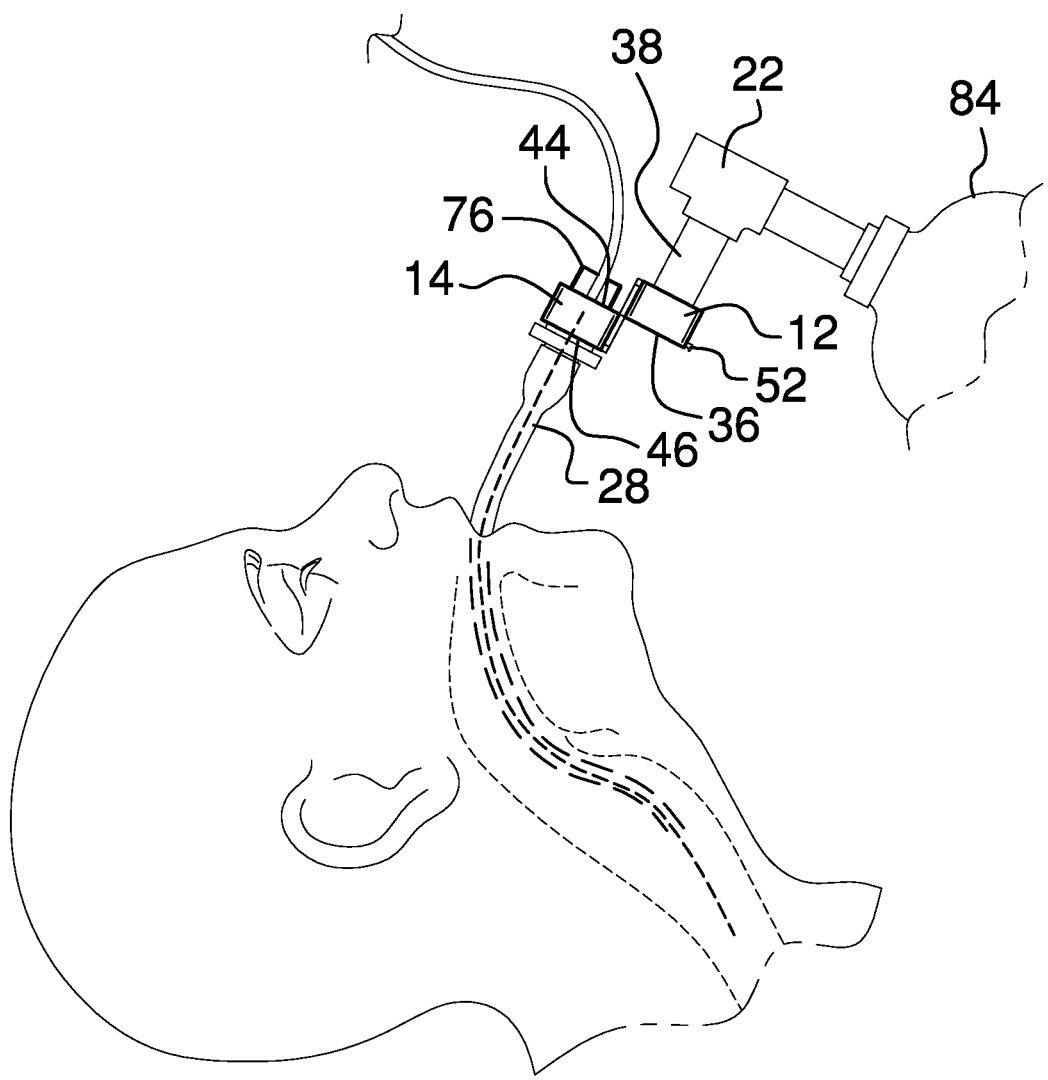
FIG. 7 is an in-use view of an embodiment of the disclosure.

In use, the associated connector 38 of the patient valve 22 of the bag valve device 24 is inserted into the first socket 40. The associated connector 46 of the endotracheal tube 28 is inserted into the second socket 48. With the endotracheal tube 28 positioned in the airway of a patient, the user is positioned to compress a bag 84 of the bag valve device 24 to supply air to the patient, as shown in FIG. 6. Should clearing of the airway of the patient be required, the user pushes up on the knob 72 to extract the pin 66 from the channel 68. The user then swivels the first tube 12 relative to the second tube 14 so that the second tube 14 is configured to insert the suction tube into the endotracheal tube 28 to clear the airway, as shown in FIG. 7.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. An endotracheal tube to bag valve device connecting assembly comprising:

a hinge;

a first tube and a second tube coupled to the hinge such that the first tube is positioned for swiveling relative to the second tube for aligning the first tube with the second tube such that the first tube and the second tube define a pipe, a first end of the pipe being configured for selectively coupling to a patient valve of a bag valve device, a second end of the pipe being configured for selectively coupling to an endotracheal tube wherein the pipe is configured for flowing of gas from the bag valve device to the endotracheal tube and such that the first tube is positioned for swiveling on the hinge wherein the second tube is configured for inserting a suction tube into the endotracheal tube for clearing an airway; and wherein the hinge comprises a first barrel coupled to the first tube, a second barrel coupled to the second tube, and a pivot extending through the first barrel and the second barrel such that the first tube is hingedly coupled to the second tube, the pivot being oriented parallel to respective central axes of said first tube and said second tube wherein said first tube swivels in a plane perpendicular to said respective central axes of said first tube and said second tube.

2. The assembly of claim 1, further comprising:

a first coupler coupled to the first end of the pipe, the first coupler being configured to be complementary to an associated connector of the patient valve of the bag valve device wherein the first coupler is configured for selectively coupling to the associated connector for coupling the pipe to the bag valve device; and a second coupler coupled to the second end of the pipe, the second coupler being configured to be complementary to an associated connector of the endotracheal tube wherein the second coupler is configured for selectively coupling to the associated connector for coupling the pipe to the endotracheal tube.

3. The assembly of claim 2, further including the first coupler comprising a first socket and the second coupler comprising a second socket.

4. The assembly of claim 3, further including the first socket having an inner diameter of from 5.0 to 75.0 millimeters and the second socket having an internal diameter of from 5.0 to 75.0 millimeters.

5. The assembly of claim 3, further including the first socket having an inner diameter of from 10.0 to 25.0 millimeters and the second socket having an internal diameter of from 10.0 to 25.0 millimeters.

6. The assembly of claim 3, further including the first socket having an inner diameter of 15.0 millimeters and the second socket having an internal diameter of 15.0 millimeters.

7. The assembly of claim 1, further comprising:
a first fastener coupled to a lower end of the first tube; and
a second fastener coupled to an upper end of the second tube, the second fastener being complementary to the first fastener such that the second fastener is positioned for selectively coupling to the first fastener for fixedly coupling the second tube to the first tube for defining the pipe.

8. The assembly of claim 7, further including the second fastener and the first fastener comprising a clasp, the clasp being spring-loaded.

9. The assembly of claim 8, further including the clasp comprising:
a recess extending into the first tube adjacent to the lower end;
a spring coupled to the first tube and extending from an upper limit of the recess;
a pin coupled to the spring distal from the upper limit;
a channel extending into the second tube from the upper end such that the channel is aligned with and positioned for selectively inserting the pin; and
a knob coupled to the pin proximate to the spring such that the knob extends from the recess past a circumference of the first tube wherein the knob is configured for engaging with a digit of a hand of a user for extracting the pin from the channel positioning the user for swiveling the first tube relative to the second tube such that the second tube is configured for inserting the suction tube into the endotracheal tube for clearing the airway.

10. The assembly of claim 9, further including a protrusion coupled to an exterior surface of the second tube proximate to the upper end, the protrusion extending past the upper end wherein the protrusion is configured for guiding the suction tube into the endotracheal tube.

11. The assembly of claim 10, further including a bevel positioned in a respective opposing side of the protrusion wherein the respective opposing side is configured for sliding of the suction tube along the bevel into the endotracheal tube.

12. An endotracheal tube, bag valve device, and connecting assembly combination comprising:
an endotracheal tube;
a bag valve device;
a hinge;
a first tube and a second tube coupled to the hinge such that the first tube is positioned for swiveling relative to the second tube for aligning the first tube with the second tube such that the first tube and the second tube define a pipe, a first end of the pipe being selectively couplable to a patient valve of the bag valve device, a second end of the pipe being selectively couplable to the endotracheal tube wherein the pipe is configured for flowing of gas from the bag valve device to the endotracheal tube and such that the first tube is positioned for swiveling on the hinge wherein the second tube is configured for inserting a suction tube into the endotracheal tube for clearing an airway; and
wherein the hinge comprises
a first barrel coupled to the first tube,
a second barrel coupled to the second tube, and
a pivot extending through the first barrel and the second barrel such that the first tube is hingedly coupled to the second tube, the pivot being oriented parallel to respective central axes of said first tube and said second tube wherein said first tube swivels in a plane perpendicular to said respective central axes of said first tube and said second tube.

13. An endotracheal tube to bag valve device connecting assembly comprising:
a first tube and a second tube coupled to a hinge such that the first tube is positioned for swiveling relative to the second tube for aligning the first tube with the second tube such that the first tube and the second tube define a pipe, a first end of the pipe being configured for selectively coupling to a patient valve of a bag valve device, a second end of the pipe being configured for selectively coupling to an endotracheal tube wherein the pipe is configured for flowing of gas from the bag valve device to the endotracheal tube and such that the first tube is positioned for swiveling on the hinge wherein the second tube is configured for inserting a suction tube into the endotracheal tube for clearing an airway, the hinge comprising:
a first barrel coupled to the first tube,
a second barrel coupled to the second tube, and
a pivot extending through the first barrel and the second barrel such that the first tube is hingedly coupled to the second tube, the pivot being oriented parallel to respective central axes of said first tube and said second tube wherein said first tube swivels in a plane perpendicular to said respective central axes of said first tube and said second tube;
a first coupler coupled to the first end of the pipe, the first coupler being complementary to an associated connector of the patient valve of the bag valve device wherein the first coupler is configured for selectively coupling to the associated connector for coupling the pipe to the bag valve device, the first coupler comprising a first socket, the first socket having an inner diameter of from 5.0 to 75.0 millimeters;
a second coupler coupled to the second end of the pipe, the second coupler being complementary to an associated connector of the endotracheal tube wherein the second coupler is configured for selectively coupling to the associated connector for coupling the pipe to the endotracheal tube, the second coupler comprising a second socket, the second socket having an internal diameter of from 5.0 to 75.0 millimeters;
a first fastener coupled to a lower end of the first tube;
a second fastener coupled to an upper end of the second tube, the second fastener being complementary to the first fastener such that the second fastener is positioned for selectively coupling to the first fastener for fixedly coupling the second tube to the first tube for defining the pipe, the second fastener and the first fastener comprising a clasp, the clasp being spring-loaded, the clasp comprising:
a recess extending into the first tube adjacent to the lower end,
a spring coupled to the first tube and extending from an upper limit of the recess,
a pin coupled to the spring distal from the upper limit,
a channel extending into the second tube from the upper end such that the channel is aligned with and positioned for selectively inserting the pin, and
a knob coupled to the pin proximate to the spring such that the knob extends from the recess past a circumference of the first tube wherein the knob is configured for engaging with a digit of a hand of a user for extracting the pin from the channel positioning the user for swiveling the first tube relative to the second tube such that the second tube is configured for inserting the suction tube into the endotracheal tube for clearing the airway;

a protrusion coupled to an exterior surface of the second tube proximate to the upper end, the protrusion extending past the upper end wherein the protrusion is configured for guiding the suction tube into the endotracheal tube; and a bevel positioned in a respective opposing side of the protrusion wherein the respective opposing side is configured for sliding of the suction tube along the bevel into the endotracheal tube.

* * * * *